(12) United States Patent
Shu et al.

(10) Patent No.: US 10,628,937 B2
(45) Date of Patent: Apr. 21, 2020

(54) MANAGING IDENTIFIERS OF COMPONENTS OF MEDICAL IMAGING APPARATUS

(71) Applicant: Shanghai Neusoft Medical Technology Co., Ltd., Shanghai (CN)

(72) Inventors: Qingxiang Shu, Shenyang (CN); Shuangxue Li, Shenyang (CN); Jun Yu, Shenyang (CN)

(73) Assignee: Shanghai Neusoft Medical Technology Co., Ltd., Shanghai (CN)

( * ) Notice: Subject to any disclaimer, the term of this patent is extended or adjusted under 35 U.S.C. 154(b) by 198 days.

(21) Appl. No.: 15/795,756

(22) Filed: Oct. 27, 2017

(65) Prior Publication Data
US 2018/0122059 A1 May 3, 2018

(30) Foreign Application Priority Data
Oct. 28, 2016 (CN) .......................... 2016 1 0972798

(51) Int. Cl.
| | |
|---|---|
| *G06T 7/00* | (2017.01) |
| *G16H 40/63* | (2018.01) |
| *G06F 19/00* | (2018.01) |
| *G06K 9/62* | (2006.01) |
| *H04L 9/06* | (2006.01) |

(Continued)

(52) U.S. Cl.
CPC ............ *G06T 7/001* (2013.01); *G06F 19/321* (2013.01); *G06K 9/6202* (2013.01); *G16H 40/63* (2018.01); *H04L 9/0618* (2013.01); *G06K 7/10762* (2013.01); *G06K 7/1417* (2013.01); *G06K 2209/057* (2013.01); *G06T 2207/30164* (2013.01); *G06T 2207/30204* (2013.01)

(58) Field of Classification Search
CPC .......... G06T 7/001; G06T 2207/30204; G06T 2207/30164; H04L 9/0618; G06K 9/6202; G06K 2209/057; G06K 7/1417; G06K 7/10762; G06K 19/06103; G06K 19/06037; G06F 19/321; G16H 40/63; G06Q 10/06313

See application file for complete search history.

(56) References Cited

U.S. PATENT DOCUMENTS

| | | | | |
|---|---|---|---|---|
| 8,340,453 | B1 * | 12/2012 | Chen ...................... | G06T 5/002 382/254 |
| 8,893,975 | B2 * | 11/2014 | Sanford .......... | G06K 19/06103 235/487 |
| 9,613,482 | B1 * | 4/2017 | Polk, Jr. .................... | G07F 1/06 |

(Continued)

*Primary Examiner* — Xuemei G Chen
(74) *Attorney, Agent, or Firm* — Fish & Richardson P.C.

(57) ABSTRACT

An identification device for a part of a medical imaging apparatus includes: an identifier carrier fixed to a shell of the part and storing information of an identifier of the part, a housing configured to cover the identifier carrier, an image capturing component provided on the housing, and a processor configured to control the image capturing component to capture an image and acquire the identifier of the part based on a captured image. The processor is configured to perform deviation check on a current image captured by the image capturing apparatus currently and an initial image captured by the image capturing component previously and determine whether the identifier of the part has been tampered with or replaced based on a result of the deviation check.

20 Claims, 5 Drawing Sheets

(51) Int. Cl.
*G06K 7/10* (2006.01)
*G06K 7/14* (2006.01)

(56) References Cited

U.S. PATENT DOCUMENTS

| | | | |
|---|---|---|---|
| 9,996,107 B2* | 6/2018 | Inoue | A63F 13/24 |
| 10,242,301 B2* | 3/2019 | Ophardt | A47K 5/12 |
| 2004/0171935 A1* | 9/2004 | Van Creveld | A61B 8/00 |
| | | | 600/437 |
| 2005/0240305 A1* | 10/2005 | Bogash | G06F 19/3462 |
| | | | 700/242 |
| 2008/0023553 A1* | 1/2008 | Jones | G06K 7/10712 |
| | | | 235/462.41 |
| 2009/0016574 A1* | 1/2009 | Tsukahara | A61B 5/117 |
| | | | 382/117 |
| 2010/0018330 A1* | 1/2010 | Marty | G01N 35/00732 |
| | | | 73/864.81 |
| 2011/0024505 A1* | 2/2011 | Wang | G06K 7/10722 |
| | | | 235/462.41 |
| 2016/0140429 A1* | 5/2016 | Glosser | G06K 19/06075 |
| | | | 702/185 |
| 2016/0328588 A1* | 11/2016 | Hagen | G01N 35/00732 |
| 2017/0035528 A1* | 2/2017 | Neff | A61B 90/98 |
| 2018/0007070 A1* | 1/2018 | Kulkarni | H04L 63/1416 |
| 2018/0096179 A1* | 4/2018 | Dang | G01S 5/02 |
| 2019/0085616 A1* | 3/2019 | Soufflet | E05B 47/0001 |

* cited by examiner

MANAGING IDENTIFIERS OF COMPONENTS OF MEDICAL IMAGING APPARATUS

CROSS REFERENCE TO RELATED APPLICATIONS

This application claims priority to Chinese Patent Application No. 201610972798.5 filed on Oct. 28, 2016, the entire content of which is incorporated herein by reference.

TECHNICAL FIELD

The present disclosure relates to methods, devices, and systems for managing identifiers of components of medical imaging apparatus, particularly by identification devices for the components of the medical image apparatus.

BACKGROUND

An X-ray tube (hereinafter referred to as tube) of a medical imaging apparatus such as a computed tomography (CT) apparatus is an important high-value component. However, a serial number (SN) of a tube, as a unique identifier of the tube, is usually attached to a shell of the tube in a form of a self-adhesive label. The identifier of the tube may only be read manually, which is very inconvenient. For this reason, the SN of the tube may also be written into a programmable chip which may be fixed to the shell of the tube by screws. In this way, systems inside and outside a factory including the CT apparatus itself may read the identifier of the tube electronically.

However, there is a problem that the identifier may be replaced, whether the identifier is attached on the shell of the tube in the form of a self-adhesive label or the programmable chip is fixed to the shell of the tube by screws. As a result, one unique identifier may not correspond to a single tube, which makes it difficult to manage and trace tubes, and hence may lead to business disputes and may even cause losses to the CT manufacturers. For example, during a warranty period, a third party may replace the tube and attach the label of the original tube to a tube of a third party. This causes that the CT manufacturer is unable to determine the source of the tube only by the label, and hence is still responsible for the warranty of the replaced tube.

In addition to an X-ray tube, there may be similar problems with other parts of a medical imaging apparatus.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods, devices, and systems for managing an identifier of a component (or part) of medical imaging apparatus, which can support electronic reading of the identifier and prevent the identifier from being tampered with or replaced to thereby realize unique correspondence between the identifiers and the components and facilitate management and tracing of the components.

One aspect of the present disclosure features an identification device for a part of a medical imaging apparatus, including: an identifier carrier arranged on a shell of the part and configured to store information of an identifier of the part; a housing configured to cover the identifier carrier; an image capturing component provided on the housing; and a processor configured to: control the image capturing component to capture a current image, acquire the identifier of the part based on the captured current image, and perform a deviation check on the current image captured by the image capturing component currently and an initial image captured by the image capturing component previously.

The processor can be configured to determine whether the identifier of the part has been tampered with or replaced based on a result of the deviation check. In some cases, the processor is configured to: perform the deviation check by determining whether a deviation value between the initial image and the current image exceeds a predetermined threshold, and determine that the identifier of the part has been tampered with or replaced in response to a determination that the deviation value exceeds the predetermined threshold.

The identification device can further include a memory configured to prestore the initial image. The initial image can include a factory image captured by the image capturing component after the part is provided with the identifier carrier. In some implementations, the housing includes a shading housing, and the image capturing component contains a light source, and the memory is configured to prestore a capturing parameter of the image capturing component for capturing the initial image, and the processor is configured to control the image capturing component to capture the current image with the prestored capturing parameter.

The image capturing component is configured to capture the current image within an image capturing range which covers the identifier carrier and a preset range around the identifier carrier. The identification device can further include an anti-replacement marker arranged in the preset range and configured to be moved together with the housing.

In some cases, the processor is configured to: perform the deviation check by checking a positional deviation of the anti-replacement marker in the current image and the initial image, and determine that the identifier of the part has been tampered with or replaced in response to a determination that the positional deviation exceeds the predetermined threshold.

In some implementations, the housing is fixed on the shell of the part by one or more fasteners. In some cases, at least one of the fasteners is located in the preset range and provided with a gasket with a pattern, and at least a portion of the gasket is located inside the housing and the gasket with the pattern serves as the anti-replacement marker. In some cases, at least one of the fasteners is located in the preset range and provided with a gasket with a pattern, and the gasket with the pattern and a thread of the fastener close to the gasket together serves as the anti-replacement marker, and at least a portion of the gasket and a portion of the thread is located inside the housing.

The information of the identifier of the part can include cipher data of the identifier of the part after encryption, and the processor can be configured to decode the identifier carrier in the current image to acquire the cipher data and decrypt the cipher data to acquire the identifier of the part. The identifier carrier can include a two-dimensional code, and the two-dimensional code can be formed on the shell of the part by marking.

Another aspect of the present disclosure features a medical imaging component of a medical imaging apparatus, including: a main body, an identifier carrier arranged on a shell of the main body and configured to store information of an identifier of the main body, a housing configured to cover the identifier carrier, and an image capturing component provided on the housing and configured to capture an image under a control of a processor configured to acquire the identifier of the main body based on the captured image. The medical imaging apparatus can be a CT apparatus, and the main body can include a tube.

The housing can include a shading housing, and the image capturing component can contain a light source. The image capturing component can be configured to capture the image within an image capturing range that covers the identifier carrier and a preset range around the identifier carrier, and an anti-replacement marker can be provided in the preset range and moved along with the housing.

In some cases, the housing is fixed on the shell of the part by a plurality of fasteners. At least one of the fasteners is located in the preset range and provided with a gasket with a pattern, and at least a portion of the gasket is located inside the housing, and the anti-replacement marker can include at least one of the gasket with the pattern or a thread of the fastener close to the gasket.

In some cases, the information includes cipher data of the identifier of the main body after encryption, and the processor is configured to decode the identifier carrier in the current image to acquire the cipher data and decrypt the cipher data to acquire the identifier of the main body. In some cases, the identifier carrier includes a two-dimensional code, and the two-dimensional code is formed on the shell by marking.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

A medical imaging apparatus can include a number of parts (or components). To facilitate understanding and explanation, a tube, which is a high value part in a CT apparatus, is taken as an example to illustrate a specific structure of an identification device of the present disclosure. It is to be understood that identification devices for other parts in medical imaging apparatuses are similar therewith, description of which is omitted. Note that the terms "component" and "part" can be used interchangeably herein.

Figure 1:
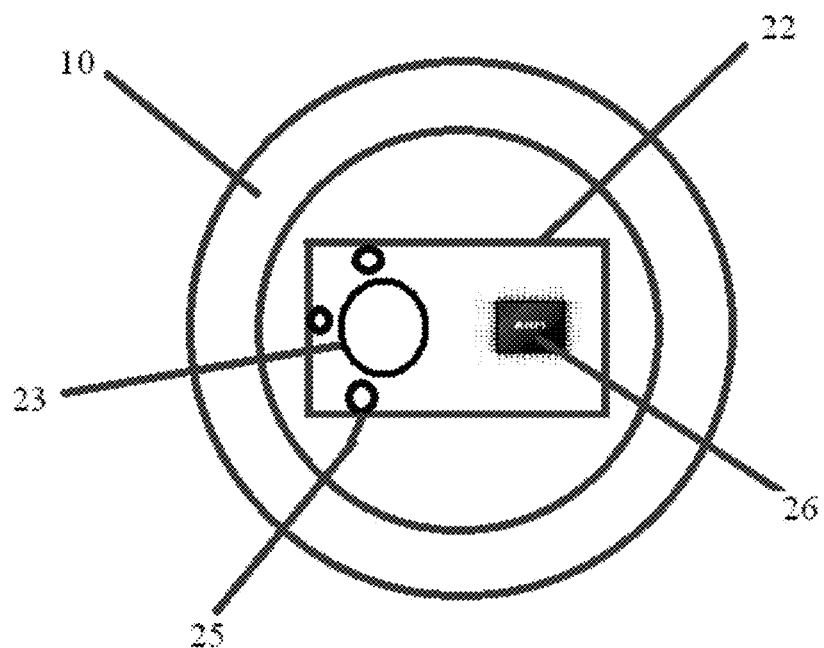
FIG. 1 is a structural diagram of an identification device for a tube of a CT apparatus according to an example of the present disclosure.
Figure 2:
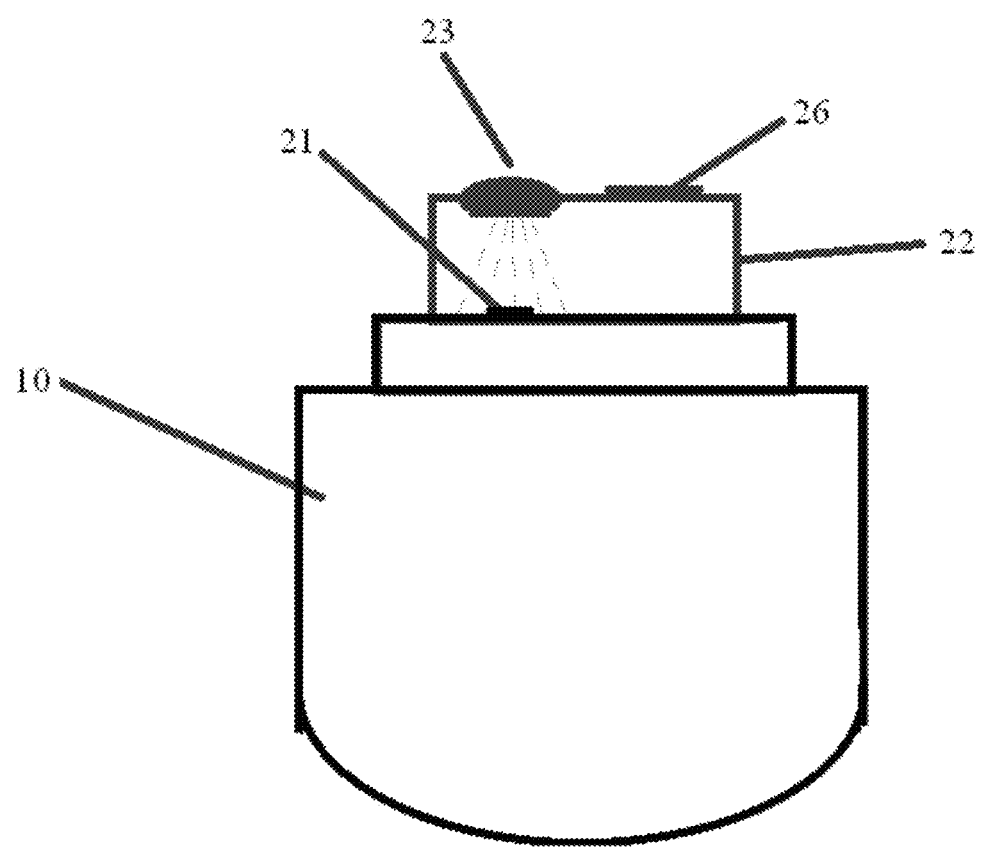
FIG. 2 is a structural diagram of the identification device in FIG. 1 from another angle.
Figure 3:
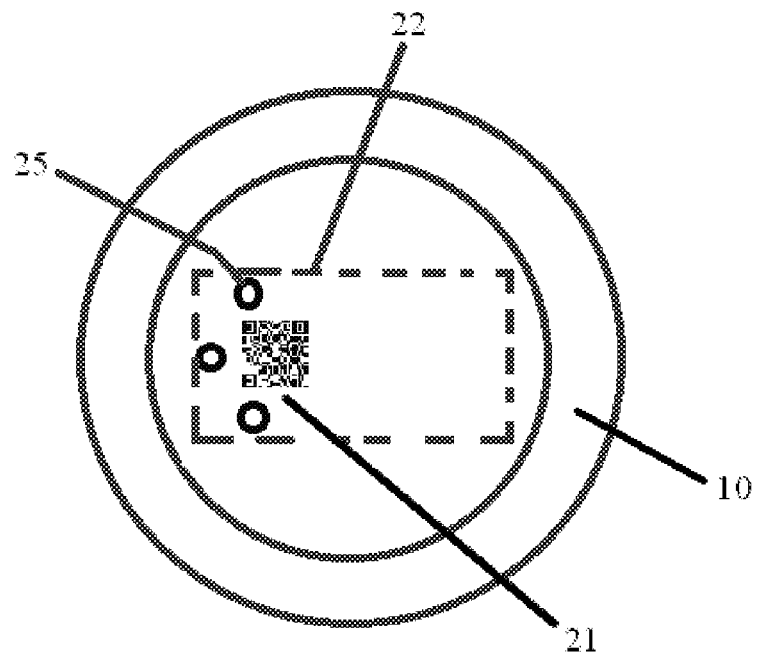
FIG. 3 is a schematic diagram showing relative positions of a two-dimensional code of a tube, a shading housing and gaskets according to an example of the present disclosure.

Referring to FIGS. 1-3, FIG. 1 is a structural diagram of an identification device for a tube 10 of a CT apparatus according to an example of the present disclosure, FIG. 2 is a structural diagram of the identification device for the tube of the CT apparatus in FIG. 1 from another angle, and FIG. 3 is a schematic diagram showing relative positions of a two-dimensional code of the tube, a shading housing and gaskets according to an example of the present disclosure.

In the example, the identification device for the tube 10 of the CT apparatus may include an identifier carrier arranged on a shell of the tube 10, which may store information corresponding to an identifier of the tube 10. For example, the identifier carrier may be a two-dimensional code 21 (see FIGS. 2 and 3). The two-dimensional code 21 may be formed by marking on the shell of the tube 10. For example, laser marking technology may be used.

The shell of the tube 10 may be provided with a housing 22, and the housing 22 may cover the two-dimensional code 21. For example, after the housing 22 is fixed to the shell of the tube 10, the two-dimensional code 21 may be located within the housing 22.

An image capturing component may also be provided on the housing 22 to capture an image of an interior of the housing 22. According to an example, the image capturing component may be a camera 23. An image capturing range of the camera 23 may include the two-dimensional code 21 and a preset range around the two-dimensional code 21. An anti-replacement marker may be provided within the preset range, which may be configured to be moved along (or together) with the housing 22. For example, after the housing 22 is fixed to the tube 10, if the housing 22 is to be removed or moved, the anti-replacement marker may also be moved along with the housing 22, thus it may be determined whether the identifier of the tube 10 has been tampered with or replaced according to a position change of the anti-replacement marker.

A processor may be configured to control the camera 23 to capture a current image and acquire (or determine) the identifier of the tube 10 based on the captured current image.

For example, the processor may be fixed on the housing 22 and communicatively connected with the CT apparatus. The processor may also be embedded within the CT apparatus.

To enable the image capturing range of the camera 23 to cover the two-dimensional code 21 and the anti-replacement marker, the camera 23 may be installed on a side of the housing 22 away from the shell of the tube 10, and a height from the camera 23 to the shell of the tube 10 may be larger than a minimum capturable distance of the camera 23.

The processor may also perform a deviation check on a current image and an initial image captured by the camera 23.

As mentioned above, when the identifier of the tube 10 is to be identified, the processor may call the camera 23 to capture a current image, and acquire the identifier of the tube 10 according to the two-dimensional code 21 in the captured current image. Further, the processor may also perform a deviation check on the current image and the initial image captured by the camera 23. If it is found that a deviation value between the two images exceeds a preset threshold after the check, it may be determined that the identifier of the tube 10 has been tampered with or replaced.

Because the anti-replacement marker is provided in the image capturing range of the camera 23, it may be determined whether the identifier of the tube 10 (for example, the two-dimensional code 21) has been tampered with or replaced by determining whether a position of the anti-replacement marker in the current image is changed. For example, the processor may check a positional deviation of the anti-replacement marker in the two images when performing a deviation check of the two images. The tube 10 with the identification device may not only support electronic reading of the identifier, but also prevent the identifier from being tampered with or replaced, thus realizing unique correspondence between the identifier and the tube 10 effectively and facilitating management and tracing of the tube 10 of the CT apparatus.

According to an example, a memory may also be provided, and the memory may also be embedded within the CT apparatus. The memory may be configured to prestore the initial image captured by the camera 23 therein. The initial image may be a factory image captured by the camera 23 after the tube 10 is provided with the identification device, and may cover the two-dimensional code 21 and the anti-replacement marker.

In this way, the processor may determine whether the identifier of the tube 10 has been tampered with or replaced, while identifying the two-dimensional code 21 to acquire the identifier of the tube 10, which is convenient and reliable.

Furthermore, the housing 22 may be designed as a shading housing, and the camera 23 may include a light source. One or more capturing parameters of the camera 23 when capturing the initial image may be prestored in the memory. Thus, when the processor controls the camera 23 to capture a current image, the current image may be captured with the capturing parameters stored in the memory.

In this way, this configuration may not only prevent information of the two-dimensional code 21 and the anti-replacement marker from being acquired from outside, but also ensure brightness and definition of the captured image effectively because the camera 23 is equipped with a light source. Moreover, since the capturing parameters of the camera 23 when capturing a subsequent image and the initial image are the same, an accuracy of a subsequent deviation check may be ensured.

For example, the capturing parameters may include an illumination angle and intensity of the light source, the operating parameters of the camera 23, etc., which may be set according to an actual situation.

Data stored in the two-dimensional code 21 may be cipher data of the encrypted unique identifier of the tube 10. Accordingly, the processor may decode the two-dimensional code in the image captured by the camera 23 to acquire the cipher data, and decrypt the cipher data to acquire the identifier of the tube 10.

The processor may include a signal receiving and transmitting module for receiving a signal for calling the camera 23, sending a capturing signal to the camera 23, receiving an image captured by the camera 23, sending a signal corresponding to a result of a deviation check, and so on.

The processor may also include a decoding module for decoding the two-dimensional code 21 in a received image. For example, the decoding module may be a two-dimensional code decoding chip 26. The two-dimensional code decoding chip 26 is fixed on the housing 22 in the example as shown in the accompanying figures. It is to be understood that the two-dimensional code decoding chip 26 may be integrated with the signal receiving and transmitting module and other modules of the processor. For example, the decoding module may also be a two-dimensional code decoding software in the CT apparatus.

The processor may also include an image checking module to perform a deviation check on the initial image and a current image. For example, a deviation threshold may be set according to an actual requirement. If a deviation between the current image and the initial image exceeds the set deviation threshold, the processor may output a signal indicating that the identifier has been tampered with or replaced; if the set deviation threshold is not exceeded, the processor may output a signal indicating the identifier has not been tampered with or replaced.

Figure 4:
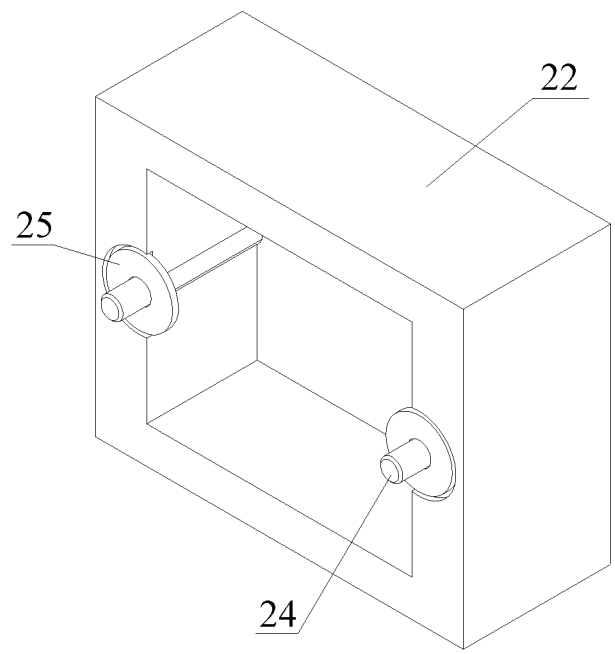
FIG. 4 shows an axonometric diagram of a shading housing of an identification device according to an example of the present disclosure.

The housing 22 may be fixed on the shell of the tube 10 through a plurality of fasteners. For example, as shown in FIG. 4, the fasteners may be screws 24, which are simple and reliable.

One or more of the screws 24 may each be provided with a gasket 25, whose surface may be provided with a random pattern. Thus, the gasket 25 may be used as the aforementioned anti-replacement marker. Obviously, the gasket 25 with the random pattern may be located in the image capturing range of the camera 23. It is to be noted that the random pattern here may mean that number and content of the pattern set on the gasket 25 are random, and/or arrangement of the pattern is random.

It is noted that the random pattern of the gasket 25 means that for different tubes 10 the patterns on surfaces of the gaskets 25 are different, so that the identifier may be prevented from being tampered with or replaced. If patterns on the surfaces of the gaskets 25 used as anti-replacement markers are uniform, the gaskets are easy to be forged.

Of course, patterns on the surfaces of the gaskets 25 may include not only the above random patterns, but also preset patterns. For example, the patterns may be predesigned for different tubes 10 with different identifiers.

FIG. 1 and FIG. 3 exemplarily show structures with three gaskets 25. The number of gaskets 25 that act as anti-replacement markers may also be randomly set. Of course, there may be at least one gasket. When two or more gaskets 25 are set, positions of the gaskets 25 may also be random, so as to make the anti-replacement markers more obvious and facilitate the deviation check on images.

In particular, the gaskets 25 may be fully located inside the housing 22. For example, after the housing 22 is fixed to the shell of the tube 10, the gaskets 25 may not be seen from outside, for example, no portions of the gaskets 25 will extend beyond an outer edge of the housing 22. Thus, a case may be prevented where a person without authorization may press the gaskets 25 to fix the positions of the gaskets 25 when removing or moving the housing 22.

Figure 5:
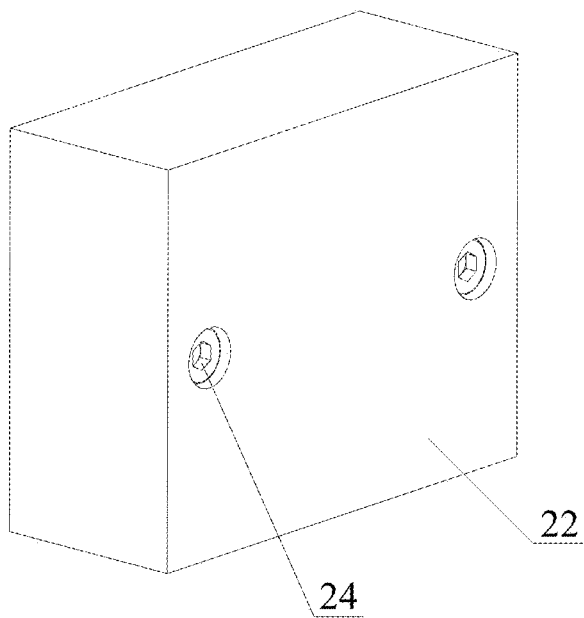
FIG. 5 is an axonometric diagram of the shading housing in FIG. 4 from another angle.
Figure 6:
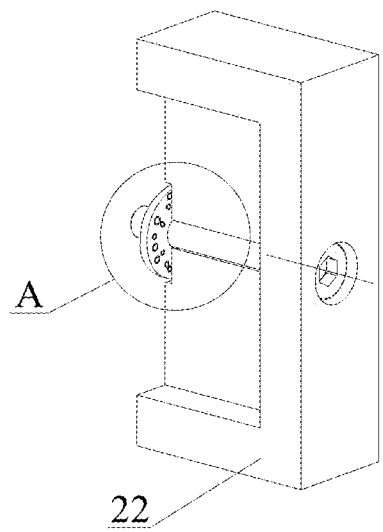
FIG. 6 is a section view of the shading housing in FIG. 4.
Figure 7:
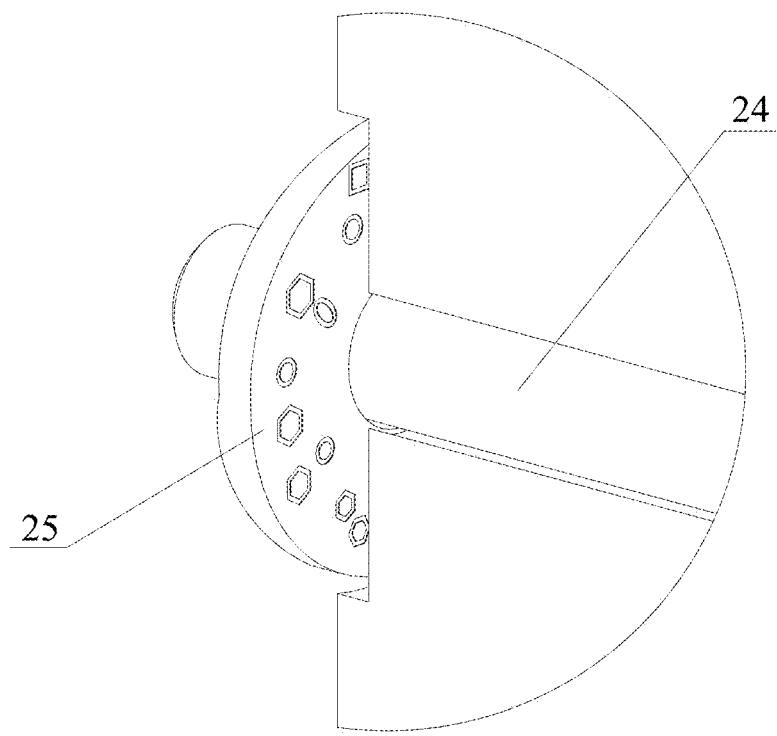
FIG. 7 is a partial enlarged view of part A in FIG. 6.

Referring to FIGS. 4-7, FIG. 4 shows an axonometric diagram of the shading housing of the identification device according to an example, FIG. 5 is an axonometric diagram of the shading housing in FIG. 4 from another angle, FIG. 6 is a section view of the shading housing in FIG. 4, and FIG. 7 is a partial enlarged view of part A in FIG. 6. In the example as shown in the figures, the shading housing 22 substantially has a shape of rectangular prism and is provided with two sets of screws 24 and gaskets 25, for example.

To ensure fixation of the housing 22 and the shell of the tube 10, one or more of the screws 24 may be far away from the two-dimensional code 21, e.g., beyond the image capturing range of the camera 23. Thus gaskets 25 may not be provided on these screws 24, or common gaskets may be provided on these screws 24. To make the gaskets 25 with anti-replacement function appear in the image capturing range of the camera 23, at least one of the screws 24 may be set on the housing 22 within the image capturing range of the camera 23. In addition to anti-replacement function, the at least one of the screws 24 may also play a role of reinforcing the housing 22 and the shell of the tube 10.

It is noted that the gaskets 25 may be partially covered by the housing 22. Of course, the gaskets 25 may not extend beyond the outer edge of the housing 22. For example, partial gaskets may be within the preset range as aforementioned, so as to be captured by the camera 23, as shown in FIG. 7.

Figure 8:
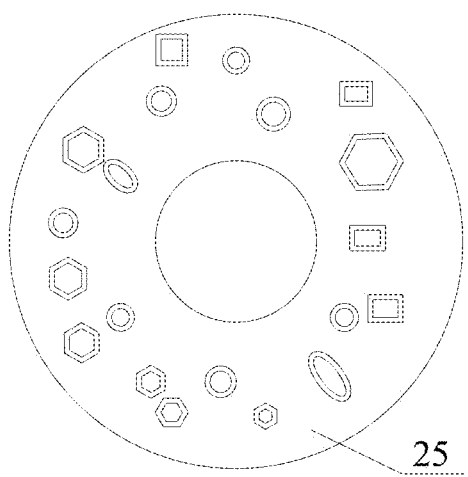
FIGS. 8 and 9 are structural diagrams of two kinds of gaskets, respectively, according to an example of the present disclosure.
Figure 9:
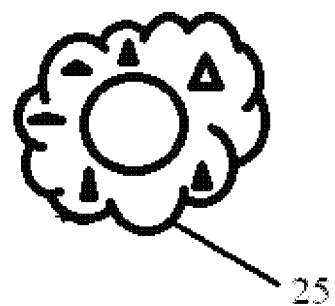

FIGS. 8 and 9 show structural diagrams of two kinds of gaskets, respectively.

According to an example of the present disclosure, shapes of the gaskets 25 may also be set randomly and variously. As shown in FIG. 8, the gasket 25 is of a circular shape, and a plurality of geometric patterns may be arranged irregularly thereon. As shown in FIG. 9, the outer circumference of the gasket 25 is irregularly shaped, and the patterns thereon are randomly arranged.

It is to be understood that the patterns of the gaskets 25 are random and not limited to the above two kinds. In addition, the shapes of the gaskets 25 may also be elliptical or polygonal.

According to an example of the present disclosure, the random patterns on the gaskets 25 may be formed by laser engraving, stamping or printing.

The camera 23 may also capture threaded portions of one or more screws 24 near the gaskets 25 when capturing an image, so that threads of the one or more screws 24 may also be checked. For example, the gaskets 25 and the threads of the one or more screws 24 near the gaskets 25 may serve as the anti-replacement markers together. When performing a deviation check on images, on the basis of identification of the gaskets 25, the captured threaded portions of the one or more screws 24 may also be checked. In this way, it is easier to determine whether the housing 22 is disassembled and whether the identifier has been tampered with or replaced.

Also provided is a part (or component) of a medical imaging apparatus, including a main body of the part and an identification device as described above. The identification device is arranged on the main body of the part to play a role of preventing the part from being tampered with or replaced. For ease of understanding and explanation, an example where the part is a tube of a CT apparatus is set forth below. It is to be understood that identification devices for other parts in medical imaging apparatuses are similar therewith, description of which is omitted.

The identification device for a part of a medical imaging apparatus has been described in detail above. Specific examples are used to illustrate the principles and the implementation of the present disclosure, and are only used to help understand the methods and the concept of the present disclosure. It will be appreciated by a person skilled in the art that numerous variations and/or modifications may be made to the above-described examples, without departing from the general scope of the present disclosure and these variations and/or modifications are within the scope of the present disclosure.

The invention claimed is:

1. An identification device for a part of a medical imaging apparatus, comprising:
    an identifier carrier arranged on a shell of the part and configured to store information of an identifier of the part;
    a housing provided on the shell of the part and configured to cover the identifier carrier;
    an image capturing component provided on the housing; and
    a processor configured to:
        control the image capturing component to capture a current image,
        acquire the identifier of the part based on the captured current image, and
        perform a deviation check on the current image captured by the image capturing component currently and an initial image captured by the image capturing component previously.

2. The identification device of claim 1, wherein the processor is configured to:
    determine whether the identifier of the part has been tampered with or replaced based on a result of the deviation check.

3. The identification device of claim 1, wherein the processor is configured to:
    perform the deviation check by determining whether a deviation value between the initial image and the current image exceeds a predetermined threshold, and
    determine that the identifier of the part has been tampered with or replaced in response to a determination that the deviation value exceeds the predetermined threshold.

4. The identification device of claim 1, further comprising a memory configured to prestore the initial image.

5. The identification device of claim 4, wherein the housing comprises a shading housing, and the image capturing component contains a light source, and
    wherein the memory is configured to prestore a capturing parameter of the image capturing component for capturing the initial image, and the processor is configured to control the image capturing component to capture the current image with the prestored capturing parameter.

6. The identification device of claim 1, wherein the image capturing component is configured to capture the current image within an image capturing range which covers the identifier carrier and a preset range around the identifier carrier.

7. The identification device of claim 6, further comprising:
    an anti-replacement marker arranged in the preset range and configured to be moved together with the housing.

8. The identification device of claim 7, wherein the processor is configured to:
    perform the deviation check by checking a positional deviation of the anti-replacement marker in the current image and the initial image, and
    determine that the identifier of the part has been tampered with or replaced in response to a determination that the positional deviation exceeds a predetermined threshold.

9. The identification device of claim 7, wherein the housing is fixed on the shell of the part by one or more fasteners.

10. The identification device of claim 9, wherein at least one of the fasteners is located in the preset range and provided with a gasket with a pattern, and at least a portion of the gasket is located inside the housing and
  wherein the gasket with the pattern serves as the anti-replacement marker.

11. The identification device of claim 9, wherein at least one of the fasteners is located in the preset range and provided with a gasket with a pattern, and
  wherein the gasket with the pattern and a thread of the fastener close to the gasket together serves as the anti-replacement marker, and at least a portion of the gasket and a portion of the thread is located inside the housing.

12. The identification device of claim 1, wherein the information of the identifier of the part comprises cipher data of the identifier of the part after encryption, and
  wherein the processor is configured to decode the identifier carrier in the current image to acquire the cipher data and decrypt the cipher data to acquire the identifier of the part.

13. The identification device of claim 1, wherein the identifier carrier comprises a two-dimensional code, and the two-dimensional code is formed on the shell of the part by marking.

14. A medical imaging component of a medical imaging apparatus, comprising:
  a main body;
  an identifier carrier arranged on a shell of the main body and configured to store information of an identifier of the main body;
  a housing provided on the shell of the main body and configured to cover the identifier carrier; and
  an image capturing component provided on the housing and configured to capture an image under a control of a processor configured to acquire the identifier of the main body based on the captured image.

15. The medical imaging component of claim 14, wherein the housing comprises a shading housing, and the image capturing component contains a light source.

16. The medical imaging component of claim 14, wherein the image capturing component is configured to capture the image within an image capturing range that covers the identifier carrier and a preset range around the identifier carrier, and
  wherein an anti-replacement marker is provided in the preset range and moved along with the housing.

17. The medical imaging component of claim 16, wherein the housing is fixed on the shell of the main body by a plurality of fasteners,
  wherein at least one of the fasteners is located in the preset range and provided with a gasket with a pattern, and at least a portion of the gasket is located inside the housing, and
  wherein the anti-replacement marker comprises at least one of the gasket with the pattern or a thread of the fastener close to the gasket.

18. The medical imaging component of claim 14, wherein the information comprises cipher data of the identifier of the main body after encryption, and
  wherein the processor is configured to decode the identifier carrier in the captured image to acquire the cipher data and decrypt the cipher data to acquire the identifier of the main body.

19. The medical imaging component of claim 14, wherein the identifier carrier comprises a two-dimensional code, and the two-dimensional code is formed on the shell by marking.

20. The medical imaging component of claim 14, wherein the main body comprises a tube.

* * * * *